(12) United States Patent
Davagian (10) Patent No.: US 12,396,946 B1
(45) Date of Patent: Aug. 26, 2025

(54) METHODS OF TREATING GASTROINTESTINAL DISEASES AND DISORDERS

(71) Applicant: Cristcot LLC, Concord, MA (US)

(72) Inventor: Jennifer J. Davagian, Acton, MA (US)

(73) Assignee: Cristcot LLC, Concord, MA (US)

( * ) Notice: Subject to any disclaimer, the term of this patent is extended or adjusted under 35 U.S.C. 154(b) by 0 days.

(21) Appl. No.: 19/065,576

(22) Filed: Feb. 27, 2025

Related U.S. Application Data

(60) Provisional application No. 63/747,540, filed on Jan. 21, 2025, provisional application No. 63/739,846, filed on Dec. 30, 2024.

(51) Int. Cl.
*A61K 9/02* (2006.01)
*A61K 31/573* (2006.01)
*A61K 47/02* (2006.01)
*A61K 47/14* (2017.01)
*A61P 1/04* (2006.01)

(52) U.S. Cl.
CPC ............ *A61K 9/02* (2013.01); *A61K 31/573* (2013.01); *A61K 47/02* (2013.01); *A61K 47/14* (2013.01); *A61P 1/04* (2018.01)

(58) Field of Classification Search
None
See application file for complete search history.

(56) References Cited

U.S. PATENT DOCUMENTS

| | | |
|---|---|---|
| 2,975,099 A | 3/1961 | Goyan et al. |
| 3,122,475 A | 2/1964 | Johann |
| 3,122,485 A | 2/1964 | Johann |
| 4,406,896 A | 9/1983 | Higuchi et al. |
| 4,434,159 A | 2/1984 | Sekine et al. |
| 4,698,359 A | 10/1987 | Niederer et al. |
| 4,837,214 A | 6/1989 | Tanaka et al. |
| 5,002,771 A | 3/1991 | Purkaystha et al. |
| 6,114,382 A | 9/2000 | Moretti |
| 6,136,337 A | 10/2000 | Kondo et al. |
| 6,740,333 B2 | 5/2004 | Beckett et al. |
| 7,635,709 B2 | 12/2009 | Korsten et al. |
| 8,192,393 B2 | 6/2012 | Ensign |
| 10,653,623 B2 | 5/2020 | Davagian et al. |
| 11,298,515 B2 | 4/2022 | Davagian |
| 11,376,217 B2 | 7/2022 | Davagian et al. |
| 2003/0185861 A1 | 10/2003 | Hori et al. |
| 2003/0229158 A1 | 12/2003 | Chen et al. |
| 2007/0048240 A1 | 3/2007 | Slavashevich et al. |
| 2007/0282161 A1 | 12/2007 | Ferguson et al. |
| 2010/0168563 A1 | 7/2010 | Braver |
| 2010/0322875 A1 | 12/2010 | Guilbaud |
| 2014/0081311 A1 | 3/2014 | Carmeli et al. |
| 2014/0200553 A1 | 7/2014 | Johnson et al. |
| 2015/0265820 A1 | 9/2015 | Davagian et al. |
| 2018/0036235 A1* | 2/2018 | Davagian ............... A61K 47/20 |
| 2024/0197629 A1 | 6/2024 | Davagian et al. |
| 2024/0197630 A1 | 6/2024 | Davagian et al. |
| 2024/0207180 A1 | 6/2024 | Davagian et al. |
| 2024/0207181 A1 | 6/2024 | Davagian et al. |
| 2024/0207182 A1 | 6/2024 | Davagian et al. |

FOREIGN PATENT DOCUMENTS

| | | |
|---|---|---|
| CN | 1110554 A | 10/1995 |
| JP | H02-178228 A | 7/1990 |
| JP | 2008-255113 A | 10/2008 |
| JP | 5279343 B2 | 9/2013 |
| WO | WO-2010/020985 A1 | 2/2010 |
| WO | WO-2015/023811 A2 | 2/2015 |
| WO | WO-2016/145233 A1 | 9/2016 |

OTHER PUBLICATIONS

Baviskar, P. et al., "Drug Delivery on Rectal Absorption: Suppositories," Int. J. Pharm. Sci. Rev. Res., vol. 21; No. 1; 70-76 (2013).
Ding et al., "Ulcerative colitis flair induced by mesalamine suppositories hypersensitivity," World Journal of Gastroenterology, Apr. 7, 2014, 20(13):3716-3718.
FDA's "Ulcerative Colitis: Clinical Trial Endpoints Guidance for Industry," Apr. 2022 (available at www.fda.gov/regulatory-information/search-fda-guidance-documents/ulcerative-colitis-developing-drugs-treatment), 15 pages.
Ishimaru et al., "Effect of lecithin on rectal absorption of diflunisal suppositories," Yakuzaigaku, 1991, 51(2):87-92.
Moreton, R.C., "Suppository Bases, Hard Fat" in Handbook of Pharmaceutical Excipients, Pharmaceutical Press, UK, XP093114431, ISBM: 978-0-85, 369-792-3, pp. 722-726 (2009).
NCT04469686, Cristcot LLC, ClinicalTrials.gov, Phase 3 Study to Evaluate the Safety and Efficacy of Hydrocortisone Acetate Suppositories, Version 1, Jul. 9, 2020, 8 pages.
NCT04469686, Cristcot LLC, ClinicalTrials.gov, Phase 3 Study to Evaluate the Safety and Efficacy of Hydrocortisone Acetate Suppositories, Version 10, May 2, 2024, 27 pages.
NCT04469686, Cristcot LLC, ClinicalTrials.gov, Phase 3 Study to Evaluate the Safety and Efficacy of Hydrocortisone Acetate Suppositories, Version 11, Aug. 30, 2024, 8 pages.
NCT04469686, Cristcot LLC, ClinicalTrials.gov, Phase 3 Study to Evaluate the Safety and Efficacy of Hydrocortisone Acetate Suppositories, Version 12, Oct. 9, 2024, 8 pages.
NCT04469686, Cristcot LLC, ClinicalTrials.gov, Phase 3 Study to Evaluate the Safety and Efficacy of Hydrocortisone Acetate Suppositories, Version 2, Jul. 30, 2020, 8 pages.

(Continued)

*Primary Examiner* — Robert A Wax
*Assistant Examiner* — Quanglong N Truong
(74) *Attorney, Agent, or Firm* — Foley & Lardner LLP (57) ABSTRACT

Formulations comprising hydrocortisone are disclosed in a suppository for methods of treating ulcerative colitis and other gastrointestinal diseases and disorders. Administering a single hydrocortisone suppository once a day achieves remission or reduction of a symptom, optionally followed by a period of time in which the dosage is reduced.

30 Claims, 2 Drawing Sheets

(56) References Cited

OTHER PUBLICATIONS

NCT04469686, Cristcot LLC, ClinicalTrials.gov, Phase 3 Study to Evaluate the Safety and Efficacy of Hydrocortisone Acetate Suppositories, Version 3, Jan. 29, 2021, 34 pages.
NCT04469686, Cristcot LLC, ClinicalTrials.gov, Phase 3 Study to Evaluate the Safety and Efficacy of Hydrocortisone Acetate Suppositories, Version 4, May 10, 2021, 34 pages.
NCT04469686, Cristcot LLC, ClinicalTrials.gov, Phase 3 Study to Evaluate the Safety and Efficacy of Hydrocortisone Acetate Suppositories, Version 5, Jun. 17, 2021, 35 pages.
NCT04469686, Cristcot LLC, ClinicalTrials.gov, Phase 3 Study to Evaluate the Safety and Efficacy of Hydrocortisone Acetate Suppositories, Version 6, Aug. 6, 2022, 31 pages.
NCT04469686, Cristcot LLC, ClinicalTrials.gov, Phase 3 Study to Evaluate the Safety and Efficacy of Hydrocortisone Acetate Suppositories, Version 7, Aug. 17, 2022, 25 pages.
NCT04469686, Cristcot LLC, ClinicalTrials.gov, Phase 3 Study to Evaluate the Safety and Efficacy of Hydrocortisone Acetate Suppositories, Version 8, Aug. 28, 2023, 21 pages.
NCT04469686, Cristcot LLC, ClinicalTrials.gov, Phase 3 Study to Evaluate the Safety and Efficacy of Hydrocortisone Acetate Suppositories, Version 9, Feb. 5, 2024, 21 pages.
Ngo, Y. and Rambaud, J.-C., "5 Aminosalicylic Acid Enema vs Hydrocortisone Acetate Foam in Idiopathic Proctitis and Proctosigmoiditis A Randomized Multicenter Trial," Gastroenterologie Clinique et Biologique, vol. 16; No. 6; 0399-8320; PREV199294135658; Abstract only; 1992.
Rowe, R. C., et al., "Colloidal Silicon Dioxide," Handbook of Pharmaceutical Excipients, XP003016902; 188-190 (2006).
Sah et al., "Formulation Development and Release Studies of Indomethacin Suppositories," Indian Journal of Pharmaceutical Sciences, Jul.-Aug. 2008, 70(4):498-501.
Schroeder et al., Coated Oral 5-Aminosalicylic Acid Therapy for Mildly to Moderately Active Ulcerative Colitis, N. Engl. J. Med., Dec. 1, 1987, 317(26):1625-1629, abstract only.
Sutherland et al., "5-Aminosalicylic Acid Enema in the Treatment of Distal Ulcerative Colitis, Proctosigmoiditis, and Proctitis," Gastroenterology, Jun. 1987, 92(6):1894-1898.

\* cited by examiner

METHODS OF TREATING GASTROINTESTINAL DISEASES AND DISORDERS

CROSS-REFERENCE TO RELATED APPLICATIONS

This application claims priority to U.S. Provisional Application Nos. 63/739,846, filed Dec. 30, 2024 and 63/747,540, filed Jan. 21, 2025, both of which are incorporated by reference in their entireties.

BACKGROUND OF THE INVENTION

There is a need for safer and more effective hydrocortisone suppository formulations for the treatment of gastrointestinal (GI) diseases and disorders, including ulcerative colitis, Crohn's disease and inflammatory bowel disease (IBD).

SUMMARY OF THE INVENTION

An embodiment comprises a method for treating a gastrointestinal disease, preferably ulcerative colitis, comprising rectally administering once a day a single suppository comprising hydrocortisone or a salt thereof, preferably about 90 mg hydrocortisone or a pharmaceutically salt thereof (preferably the hydrocortisone acetate salt), for a period of time sufficient to achieve remission or reduction of a symptom and optionally followed by a period of administering a reduced dosage of the suppository. Preferably, the suppository is administered to the patient in the morning.

Another embodiment is a method of achieving clinical remission in a patient suffering from gastrointestinal disease, preferably ulcerative colitis, comprising rectally administering once a day a single suppository comprising hydrocortisone or a pharmaceutically acceptable salt thereof, preferably about 90 mg hydrocortisone acetate, to a patient in need thereof. Preferably, the suppository is administered to the patient in the morning.

DETAILED DESCRIPTION OF THE INVENTION

Unless otherwise specified, "a" or "an" means "one or more".

As used herein, the term "about" when used in the context of the weight of a suppository, or the amount or percent by weight of a particular ingredient in a formulation, means the absolute stated value and other values proximal to the stated value that are sufficient to achieve a formulation that has an appropriate melting temperature, stability and dissolvability for use as a suppository. Appropriate melting temperatures, stability and dissolvability for a suppository, and methods for determining such properties of a formulation (e.g., suppository), are disclosed herein. Generally, the term "about" when used in this context means the absolute stated value and other values within a range of +/−10% of the stated value.

As used herein, "morning" means within a certain amount of time from waking, for example, "morning" can mean within 4 hours of waking, within 3 hours of waking, within 2 hours of waking, or within 1 hour of waking. In another embodiment, the "morning" dose can be relative to the timing of a patient's evacuation of the contents of the bowel after waking. For example, the morning dose can be within 4 hours after evacuation of the contents of the bowel after waking, within 3 hours after evacuation of the contents of the bowel after waking, within 2 hours after evacuation of the contents of the bowel after waking, or within 1 hour after evacuation of the contents of the bowel after waking.

The term, "single suppository," means one unitary suppository.

The term "target location" means the site at which the suppository may be placed inside the rectum or anal canal for treatment.

Timing and Dosage

In accordance with one aspect of the invention, a single dosage of one suppository comprising about 90 mg hydrocortisone or a salt thereof, preferably hydrocortisone acetate, is administered. A single dosage is preferably administered each morning to a patient, but once daily administration may also occur other than the morning and including during the evening. In one embodiment, the single dosage is administered daily for a period of at least 28 days. The morning dosage may be based on the time the patient wakes up in the morning. In the alternative, the morning dosage may be timed based on evacuation of the contents of the bowel after waking up. For example, the morning dosage may be 4 hours after waking up, 3 hours after waking up, 2 hours after waking up, or 1 hour after waking up. Alternatively, it may be 4 hours after evacuation of the contents of the bowel after waking up, 3 hours after evacuation of the contents of the bowel after waking up, 2 hours after evacuation of the contents of the bowel after waking up, or 1 hours after evacuation of the contents of the bowel after waking up.

In an additional embodiment, the amount of hydrocortisone or a salt thereof included in the suppository may be greater than about 90 mg. For example, the suppository administered once a day may include about 100 mg, about 110 mg, about 120 mg, about 130 mg, about 140 mg, about 160 mg, about 170 mg, or about 180 mg. In another embodiment, two suppositories may be administered twice a day, preferably in the morning and in the evening, wherein the amount of hydrocortisone acetate in each suppository is about 90 mg, about 100 mg, about 110 mg, about 120 mg, about 130 mg, about 140 mg, about 160 mg, about 170 mg, or about 180 mg.

Treatment Methods

Formulations described herein can be used to treat ulcerative colitis, including ulcerative proctitis, flares and symptoms associated with ulcerative colitis, and active ulcerative colitis of the rectum. In an embodiment, treatment comprises rectally administering a suppository comprising hydrocortisone acetate to a patient suffering from ulcerative colitis once a day for a period of time sufficient to bring about remission or relief from one or more symptoms, preferably followed by a period of tapering in which the dosage is reduced. During an initial treatment period, the suppository may be administered until there is a reduction in one or more symptoms, such as for at least 60 days, 59 days, 58 days, 57 days, 56 days, 55 days, 54 days, 53 days, 52 days, 51 days, 50 days, 49 days, 48 days, 47 days, 46 days, 45 days, 44 days, 43 days, 42 days, 41 days, 40 days, 39 days, 38 days, 37 days, 36 days, 35 days, 34 days, 33 days, 32 days, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days or 7 days.

In one embodiment, the period of tapering is about 10 days, but optionally can be about 9, 8, 7, 6, 5, or 4 days. In an embodiment, the initial treatment period comprises rectally administering a single suppository comprising about 90 mg hydrocortisone acetate once, and the tapering period comprises administering a single suppository comprising about 90 mg hydrocortisone acetate every other day. Alternatively, tapering may comprise administering a suppository with a reduced amount of hydrocortisone acetate once a day, either in the morning or the evening, preferably in the evening. In a preferred embodiment, a single suppository is administered once a day in the morning, while during the tapering period, a single suppository is administered in the evening according to a tapering schedule. Preferably, administration of the suppository is in the morning or after evacuating the contents of the bowel. The tapering period can be any period during which a reduced dose is administered relative to an initial period, and it may optionally be a time period comprising 30 days, 29, days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, or 3 days. During a tapering period, a suppository may be administered every day with a dose that is lower than the amount given during the initial treatment period, or a suppository with the same dose given during the initial administration period may be used, but with certain days during the tapering period being skipped (e.g., every other day during a 5 day tapering period).

One embodiment relates to a method of treating a patient suffering from ulcerative colitis comprising rectally administering to the patient one suppository comprising about 90 mg hydrocortisone acetate once a day for a period of about 28 days followed by a tapering period of about 10 days during which a suppository comprising about 90 mg hydrocortisone acetate is administered every other day. In another embodiment, one suppository is administered to the patient once a day in the morning during an initial treatment period. The time period for initial treatment is preferably at least 28 consecutive days or until remission is achieved. In an embodiment, the treatment method achieves clinical remission in the patient suffering from ulcerative colitis during the initial treatment period period. Thus, in another embodiment, the method is directed to a method of achieving clinical remission for a patient suffering from ulcerative colitis.

Optionally, a tapering schedule based on the following approach may be used. For a method wherein once a day dosing is administered for 28 days, tapering begins on Day 29. On each of Days 29, 31, and 33, the patient takes a single suppository dose in the evening (with no dose at all on Days 30 and 32). On Days 34 and 35, no dose is given. On Day 36, the patient takes a single suppository dose in the evening. On Days 37 and 38 no dose is given and treatment is complete.

In an embodiment, for a method wherein twice a day dosing is administered for 28 days, tapering begins on Day 29 based on the following schedule. A single suppository is given in the evening every day for five days (Days 29, 30, 31, 32, 33) while morning suppository is skipped, followed by a skip day on Day 34 (no morning or evening suppository), and then one suppository is given in the evening on Day 35 (no morning suppository). On Day 36, one morning suppository is given and no evening suppository. On Day 37, one suppository is given in the evening on Day 37 but no morning suppository. Day 38 is the end of tapering and no further treatment is given.

Another embodiment includes tapering using a different amount of hydrocortisone or salt thereof in the suppository during the tapering period. For example, in a method where a patient receives a 90 mg hydrocortisone acetate suppository twice a day during the initial treatment period, during the tapering period the patient may take a single suppository once a day in the morning or evening with a reduced amount of hydrocortisone relative to the daily dose of the treatment period, such as for example, about 170, about 160, about 150, about 140, about 130, about 120, about 110, about 100, or about 90 mg of hydrocortisone acetate in a single suppository once a day (which his less than the 180 mg amount of hydrocortisone acetate given during the initial treatment period). Similarly, tapering in patients who are given 90 mg once a day during the initial treatment period may be accomplished by administering a suppository once a day during the tapering period with a reduced amount of hydrocortisone or a salt thereof, such as about 80 mg, about 70 mg, about 60 mg, about 50 mg, or about 40 mg. In addition, as noted above, tapering may be accomplished by alternating days of administering the suppository (skip days) with or without adjusting the amount of hydrocortisone or its salt relative to the amount given during the initial treatment. Preferably, dosing during the tapering period is in the evening.

Another embodiment relates to methods of treating ulcerative colitis at different stages of development. This may include during mild, moderate, severe, and fulminant stages. Treatment may be administered during flare ups or other active stages of ulcerative colitis. Treatment with the formulations may include administration as a rescue treatment to address flares or after a period of remission has ended. Treatment with the formulations herein may also be as a mono-therapy or they may be administered concurrently with other therapies for gastrointestinal disease.

Other embodiments of the invention further relate to methods of treating gastrointestinal diseases treatable with hydrocortisone. In one embodiment, the patient being treated suffers from ulcerative proctitis. In another embodiment, the patient being treated suffers from active ulcerative colitis of the rectum. In a further embodiment, the patient being treated suffers from a flare of ulcerative colitis.

A preferred outcome for the treatment of ulcerative colitis is clinical remission of the patient. Thus, one embodiment is directed to a method of treating ulcerative colitis. Another embodiment is directed to a method of achieving clinical remission in a patient suffering from ulcerative colitis. According to these embodiments, the patient is administered a suppository comprising 90 mg hydrocortisone acetate one time a day, wherein a single dose of the 90 mg hydrocortisone acetate suppository is administered to the patient daily for at least consecutive 28 days.

In one embodiment, a single dose is administered to the patient once a day, preferably in the morning. Without wishing to be bound by any theory, administering a suppository comprising hydrocortisone acetate in the morning may be beneficial in terms of following the body's natural levels of cortisol, since endogenous levels of cortisol may be lower in the morning. In addition, it has been unexpectedly found that rectally administering a suppository comprising about 90 mg hydrocortisone acetate once a day is as effective as rectally administering a suppository comprising about 90 mg hydrocortisone acetate twice a day in a patient suffering from ulcerative colitis. A further finding is that patients who have ulcerative colitis have lower systemic absorption of hydrocortisone from a single suppository comprising 90 mg hydrocortisone acetate administered once a day compared to healthy patients who were administered the same suppository once a day. As shown in the following table, healthy patients who were administered the 90 mg hydrocortisone acetate suppository showed the following pharmacokinetics:

|  |  | LS Mean | | Test/ | 90% | Intra- |
|---|---|---|---|---|---|---|
|  |  | Test product | Reference product | Reference Ratio | Confidence Interval of Ratio | individual CV (%) |
| $C_{max}$ (ng/ml) | n = 16 | 188.7 | 380.5 | 0.4959 | (0.4586, 0.5361) | 12.58 |
| $AUC_{0-8}$ (h · ng/mL) | n = 16 | 1055 | 2228 | 0.4737 | (0.4308, 0.5208) | 15.31 |
| $AUC_{0-t}$ (h · ng/mL) | n = 16 | 2984 | 3482 | 0.8571 | (0.7181, 1.023) | 29.01 |
| $AUC_{\infty}$ (h · ng/mL) | n = 9 | 4273 | 4111 | 1.039 | (0.8109, 1.332) | 30.97 |
| $t_{max}$ (h)* | n = 16 | 7.970 | 2.475 |  | p-value: < 0.0001 |  |

*= Wilcoxon rank sum test of Hodges-Lehman test;
n: number of subjects in the analysis;
CV: coefficient of variation,
GM: geometric mean calculated from model LS Mean;
GMR: geometric mean ratio from LS mean difference;
LS: Least squares.
Log-transformed parameter was fit by a mixed model for effects of treatment, study period, and treatment sequence.
Subject within treatment sequence was included as a random effect.
Reference = Hydrocortisone retention enema;
Test = Hydrocortisone acetate suppository.

Because patients who have ulcerative colitis may have reduced side effects due to lower systemic exposure, they may optionally be administered a higher dose than a single suppository once a day comprising 90 mg hydrocortisone acetate. For example, the amount of hydrocortisone or a salt thereof included in the suppository may be greater than about 90 mg, including about 100 mg, about 110 mg, about 120 mg, about 130 mg, about 140 mg, about 160 mg, about 170 mg, or about 180 mg. They may be administered a greater dose preferably in the morning during the initial treatment period until a symptom is reduced or remission is achieved, optionally followed by a period of reduced dosing where the time of administration of the reduced dose is in the evening.

Figure 1:
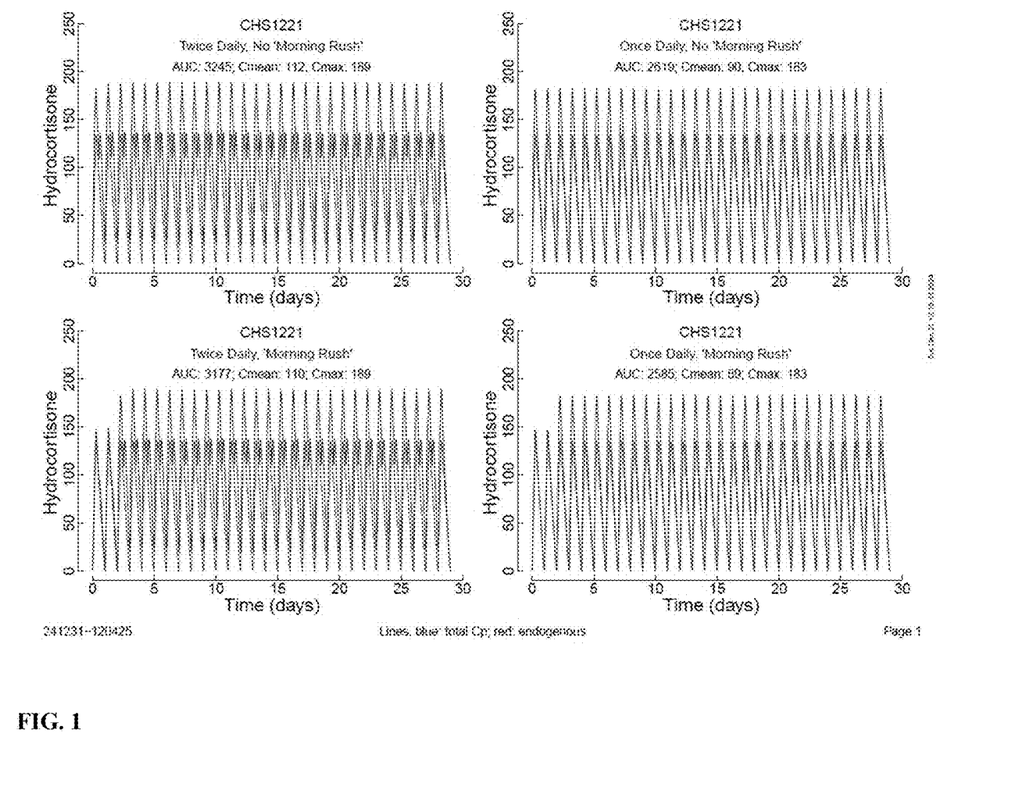
FIG. 1 shows simulated concentration of cortisol in patients during an initial treatment period with once a day or twice a day dosing of 90 mg hydrocortisone acetate suppositories.
Figure 2:
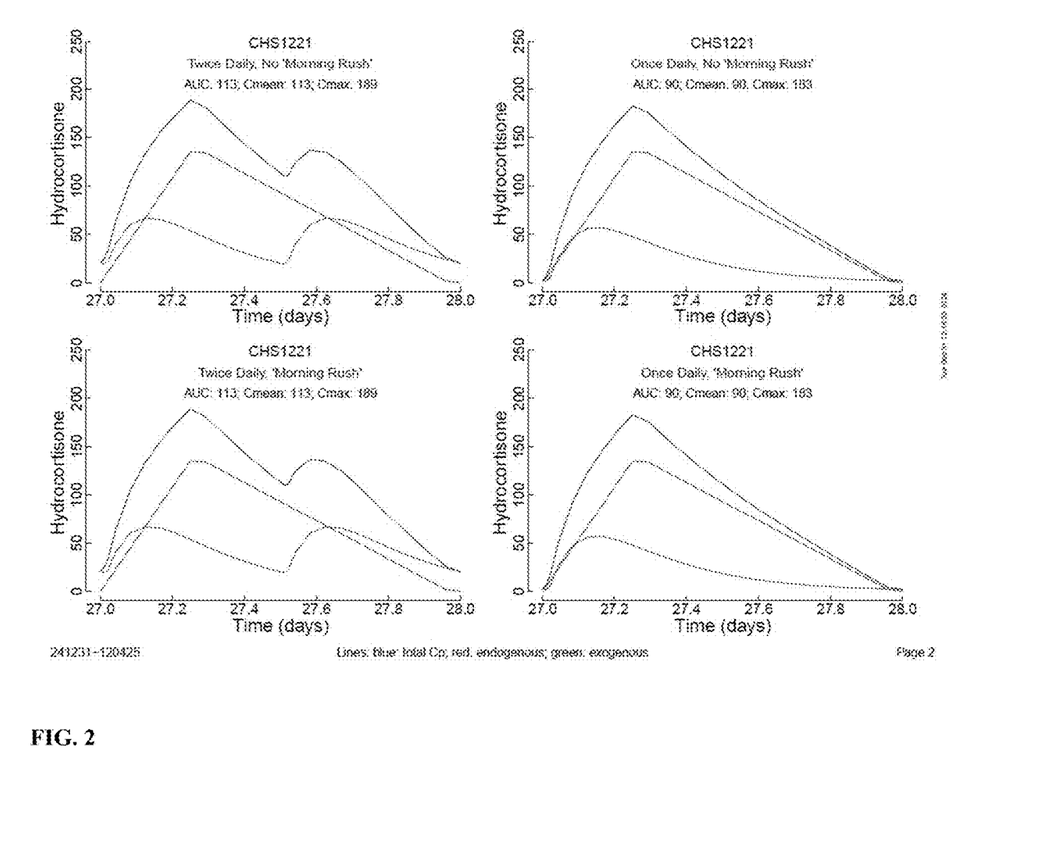
FIG. 2 shows simulated concentration at steady state of cortisol in patients at the end of an initial treatment period with once a day or twice a day dosing of 90 mg hydrocortisone acetate suppositories.

FIGS. 1 and 2 present simulated cortisol concentration results from patients with ulcerative colitis who were treated with suppositories once or twice a day comprising 90 mg hydrocortisone acetate, using a formulation of prototype 11 described below. FIG. 1 shows simulated cortisol concentration of the patients during an initial treatment period, while FIG. 2 shows simulated cortisol concentration results of patients at steady state at the end of an initial treatment period. The "morning rush" referenced in the figures means a time of day during circadian rhythm when a patient with active disease awakens and has a series of repeated and uncontrolled bowel movements until the contents of the bowel are expelled. This may include the passing of stool, water, blood and/or mucus.

In another embodiment, once a day administration of the suppository for an initial treatment period is followed by a tapering period in which one or more days there is no administration of suppository (skip day) with administration of a single suppository once a day in the morning or evening. Preferably, during the once a day tapering period, the timing of the administration is switched to evening. Surprisingly, it has been found that this tapering embodiment with evening dosing may be better than tapering with morning dosing because it follows the patient's natural (endogenous) cortisol cycle, in which a patient's natural cortisol levels are lowest in the evening as shown in FIGS. 1-2.

It has been found that clinical remission may be obtained using embodiments of the disclosed methods. Clinical remission refers to the reduction or absence of ulcerative colitis symptoms such that the disease does not interfere with their daily life. In one embodiment, clinical remission can be identified using the modified Mayo score (MMS).

The MMS score calculates the stool frequency, rectal bleeding, and endoscopy scores according to the FDA's "Ulcerative Colitis: Clinical Trial Endpoints Guidance for Industry", April 2022 (available at www.fda.gov/regulatory-information/search-fda-guidance-documents/ulcerative-colitis-developing-drugs-treatment). The primary endpoint for clinical remission using MMS scoring is as follows:
  Stool Frequency has a sub score of 0 or 1;
  Rectal Bleeding has a sub score of 0; and
  Endoscopy has a sub score of 0 or 1.
Alternatively, for the Stool Frequency sub score of 0, one may establish this endpoint if there is at least a one point decrease in Stool Frequency sub score from Baseline (start of trial) to achieve a Stool Frequency sub score of 0 or 1. These scoring techniques are well-known and established. Mayo Scoring is by Schroeder K W, Tremaine W J, and Ilstrup D M, 1987, Coated Oral 5-Aminosalicylic Acid Therapy for Mildly to Moderately Active Ulcerative Colitis, *N Engl J Med.*, 317(26): 1625-9, as follows:
Stool frequency*
*Each patient served as his or her own control to establish the degree of abnormality of the stool frequency.
  0=Normal no. of stools for this patient
  1=1-2 stools more than normal
  2=3-4 stools more than normal
  3=5 or more stools more than normal
Rectal bleeding†
†The daily bleeding score represented the most severe bleeding of the day.
  0=No blood seen
  1=Streaks of blood with stool less than half the time
  2=Obvious blood with stool most of the time
  3=Blood alone passed
Findings of flexible proctosigmoidoscopy
  0=Normal or inactive disease
  1=Mild disease (erythema, decreased vascular pattern, mild friability)

2=Moderate disease (marked erythema, absent vascular pattern, friability, erosions)

3=Severe disease (spontaneous bleeding, ulceration)

Physician's global assessment‡

‡The physician's global assessment acknowledged the three other criteria, the patient's daily record of abdominal discomfort and general sense of well-being, and other observations, such as physical findings and the patient's performance status.

0=Normal

1=Mild disease

2=Moderate disease

3=Severe disease

UCDAI Scoring is described in Sutherland L R, Martin F, Greer S, et al., 1987, 5-Aminosalicylic Acid Enema in the Treatment of Distal Ulcerative Colitis, Proctosigmoiditis, and Proctitis, *Gastroenterology*, 92:1894-8:

1. Stool frequency
   0=Normal
   1=1-2 Stools/day>normal
   2=3-4 Stools/day>normal
   3=>4 Stools/day>normal
2. Rectal bleeding
   0=None
   1=Streaks of blood
   2=Obvious blood
   3=Mostly blood
3. Mucosal appearance
   0=Normal
   1=Mild friability
   2=Moderate friability
   3=Exudation, spontaneous bleeding
4. Physician's rating of disease activity
   0=Normal
   1=Mild
   2=Moderate
   3=Severe
   Maximum score=12

Additional secondary endpoints of interest may be used to determine additional benefits of treatment as well. Using these endpoint values, it has been found that dosing a patient suffering from ulcerative colitis with a 90 mg hydrocortisone acetate suppository once a day in the morning for 28 days resulted in a greater clinical remission rate than those dosed twice a day for 28 days with the same hydrocortisone suppository.

In accordance with some embodiments, the methods of treating a patient with ulcerative colitis can further reduce the symptoms associated with ulcerative colitis. Such symptoms may include urgency, tenesmus, frequent bowel movements, diarrhea, rectal bleeding, rectal pain, abdominal pain, cramping, fever, fatigue, loss of appetite, and weight loss. Embodiments include reducing at least one symptom of ulcerative colitis, reducing at least two symptoms, at least three symptoms, at least four symptoms, at least five symptoms, at least six symptoms, at least seven symptoms, at least eight symptoms, at least nine symptoms, or at least ten symptoms of ulcerative colitis. In a preferred embodiment, at least one symptom selected from rectal bleeding, stool frequency, urgency and tenesmus is reduced in the patient being treated for ulcerative colitis. In other embodiments, the methods include reducing a modified Mayo Score in a patient suffering from ulcerative colitis. In some embodiments, the numerical value of the modified Mayo Score is reduced in one or more category selected from stool frequency, rectal bleeding, and endoscopic score.

In other embodiments, administering a 90 mg hydrocortisone acetate suppository to an ulcerative colitis patient can further reduce other measurable endpoints of interest. For example, one embodiment relates to reducing the stool frequency as scored using the MMS or UCDAI. For example, using the MMS scoring, the stool frequency may be reduced from 3 to 0, 3 to 1, 3 to 2, 2 to 0, t to 1, or 1 to 0. In another embodiment, the method can reduce rectal bleeding as scored using the MMS or UCDAI. For example, using the MMS or UCDAI scoring, the rectal bleeding may be reduced from 3 to 0, 3 to 1, 3 to 2, 2 to 0, 2 to 1, or 1 to 0. In yet another embodiment, the method can identify a reduction in the severity of the disease as scored through an endoscopy using the MMS scoring for findings of flexible proctosigmoidoscopy. Using the MMS scoring, endoscopy findings may indicate a reduction from 3 to 0, 3 to 1, 3 to 2, 2 to 0, 2 to 1, or 1 to 0. A further embodiment relates to a method to improve the mucosal appearance under the UCDAI scoring. For example, using the UCDAI scoring, the mucosal appearance may be reduced from 3 to 0, 3 to 1, 3 to 2, 2 to 0, t to 1, or 1 to 0. In addition, the method relates to a method of improve the physician's rating of ulcerative colitis disease under the MMS or UCDAI scoring. For example, using the MMS or UCDAI scoring, the physician's assessment may be reduced from 3 to 0, 3 to 1, 3 to 2, 2 to 0, 2 to 1, or 1 to 0.

Aspects of the method further include improving the Quality of Life assessment of a patient suffering from ulcerative colitis comprising administering an Inflammatory Bowel Disease Questionnaire (IBDQ) validated questionnaire to the patient, administering once a day in the morning one suppository comprising 90 mg hydrocortisone acetate to a patient in need thereof for a period of 28 days, and then administering a second IBDQ validated questionnaire for the patient after the 28 day period. According to this embodiment, the improvement of the Quality of Life assessment would be based on a reduction of one or more symptoms of ulcerative colitis.

In another aspect, the method may reduce the severity grading of a patient suffering from ulcerative colitis. According to this method, one suppository comprising 90 mg hydrocortisone acetate is administered daily to a patient in need thereof. The dose may be administered in the morning. The time period may be at least 28 days. In accordance with this aspect, the decrease in the severity grading of the disease is based on a reduction of at least one or more symptoms selected from frequent bowel movements, diarrhea, rectal bleeding, rectal pain, abdominal pain, cramping, fever, fatigue, loss of appetite, and weight loss.

The formulations (e.g., suppositories) described herein are useful for the treatment of gastrointestinal diseases and disorders, including, for example, inflammatory bowel disease (IBD), bowel ailments and other diseases for which systemic or local rectal hydrocortisone is an appropriate therapeutic intervention. Such gastrointestinal diseases and disorders include, but are not limited to, colitis (e.g., ulcerative colitis, collagenous colitis, lymphocytic colitis), Crohn's disease, proctitis (e.g., ulcerative proctitis), and hemorrhoids (e.g., internal hemorrhoids). For example, patients suffering from ulcerative proctitis, active ulcerative colitis of the rectum, and a flare up of ulcerative colitis may be treated using the methods disclosed herein.

Formulations

The formulation used in the method, in one embodiment, the formulation comprises hydrocortisone or a salt thereof, preferably about 90 mg of hydrocortisone acetate (equivalent to 80 mg hydrocortisone base). In a particular embodiment, the formulation may further comprise colloidal silicon dioxide. In a further embodiment, the formulation comprises lecithin. In some embodiments, the formulation additionally comprises an oleaginous base that includes triglycerides, for example, the formulation may comprise an oleaginous base comprising C8-C18 triglyceride fatty acids. Another embodiment relates to a formulation comprising 90 mg hydrocortisone acetate and colloid silicon dioxide. In a further embodiment, the formulation comprises 90 mg hydrocortisone acetate, colloid silicon dioxide, and lecithin. In yet another embodiment, the formulation comprises 90 mg hydrocortisone acetate, colloid silicon dioxide, lecithin, and an oleaginous based comprising C8-C18 triglyceride fatty acids. In a further embodiment, the formulation comprises 90 mg hydrocortisone acetate, colloid silicon dioxide, lecithin, and an oleaginous based comprising C10-C18 triglyceride fatty acids.

In other embodiments, the formulation is formed into a suppository having a weight of about 2 grams (g), which comprises about 90 mg hydrocortisone acetate. The suppository, according to an embodiment, releases at least about 80% of the hydrocortisone acetate at about 180 minutes following exposure to dissolution media comprising a buffered 5% w/v sodium lauryl sulfate solution having a final pH in the range of about 6.8-7.0. In additional embodiments, the suppository comprises 90 mg hydrocortisone acetate and colloidal silicon dioxide. In a particular embodiment, the suppository comprises about 90 mg hydrocortisone acetate, colloidal silicon dioxide, and an oleaginous base that includes C8-C18 triglyceride fatty acids. In another embodiment, the suppository comprises about 90 mg hydrocortisone acetate, colloidal silicon dioxide, an oleaginous base that includes C10-C18 triglycerides, and lecithin. In a particular embodiment, the suppository weighs about 2 g. In another embodiment, the suppository further comprises silicon dioxide. In a further embodiment, the suppository comprises an oleaginous base and lecithin. In other embodiments, the suppository may comprise a synthetic or biodegradable polymer impregnated with a medication. Alternatively, the suppository may be made of a metal with a polymer coating that is impregnated with the medication. In another embodiment, the suppository may comprise a water-soluble base in combination with the drug. In yet another embodiment, the suppository may encase or coat the drug in a water soluble film or coating.

The suppository is formulated to allow for the dissolution, melting and release of the hydrocortisone acetate when the suppository is placed at the target location. In particular, when the suppository is placed in the body, it dissolves and melts to allow for release of the medication. Preferably, the Cmax plasma concentrations of hydrocortisone following administration of the suppository is lower than the corresponding Cmax following administration of hydrocortisone as an enema and preferably the Tmax of the suppository is longer than the corresponding Tmax following administration of hydrocortisone as an enema. In a preferred embodiment, the hydrocortisone maximum plasma concentrations (Cmax) following administration is approximately 60% of that observed following administration of hydrocortisone as an enema. Preferably, the Tmax is about 8 hours. Preferably, the area under the concentration time curve (AUC) for the first 8 hours (AUC0-8) following administration of hydrocortisone acetate administered as a suppository is approximately 60% of the AUC0-8 observed following administration of hydrocortisone as an enema.

In one embodiment, the 90 mg hydrocortisone acetate suppository formulation may include additional elements that aid in the formulation, delivery, and/or structural composition of the hydrocortisone suppository. For example, the suppository formulation further comprises about 0.001% to about 5% by weight colloidal silicon dioxide. For example, the formulation can comprise about 0.002% to about 1%, about 0.003% to about 0.1%, about 0.004% to about 0.05%, about 0.4% to about 1.5%, or about 0.5% to about 1.0% by weight colloidal silicon dioxide. In another embodiment, the formulation comprises about 0.1% to about 5% by weight colloidal silicon dioxide. In a particular embodiment, the formulation comprises about 0.7% (e.g., 0.6%, 0.7%, 0.8%) by weight colloidal silicon dioxide.

In additional embodiments, the formulation further comprises a pharmaceutically-acceptable excipient (e.g., a pharmaceutically-acceptable excipient other than colloidal silicon dioxide). In some embodiments, the formulation comprises a pharmaceutically-acceptable excipient that is an oleaginous base. The oleaginous base can be naturally occurring, semi-synthetic or synthetic. In certain embodiments, the oleaginous base includes glycerides (e.g., monoglycerides, diglycerides and triglycerides). For example, the oleaginous base can include a mixture of monoglycerides, diglycerides and triglycerides, in a variety of ratios. In a particular embodiment, the oleaginous base includes triglycerides (e.g., more than 50% of the glyceride content is triglycerides).

Suitable oleaginous bases for use in the formulations described herein include, for example, *theobroma* oil/cocoa butter, triglycerides from vegetable oils, hydrogenated coco-glycerides, trilaurin triglycerides (glycerol trilaurate, glyceryl trilaurate, glyceryl tridodecanoate, glycerin trilaurate and tridodecanoin), lecithin and hydrogenated lecithin, synthetic or semi-synthetic triglycerides and mixtures thereof. In some embodiments, the formulation includes triglycerides from a hydrogenated vegetable oil. The vegetable oil can be, e.g., a palm oil, a palm kernel oil, a cottonseed oil, a soybean oil, a rapeseed oil, a coconut oil, a peanut oil, a sunflower seed oil or an olive oil. In other embodiments, the oleaginous base is a semi-synthetic glyceride base comprising saturated C8-C18 triglyceride fatty acids and lecithin. In a particular embodiment, the oleaginous base comprises at least about 85% triglycerides, and further comprises diglycerides and monoglycerides (e.g., less than about 15% diglycerides and less than about 1% monoglycerides). Examples of commercially available oleaginous bases that are useful for the formulations described herein include, for example, WECOBEE® M bases, HYDRO-KOTE® C and 112 bases, WITEPSOL® H-15 bases, and SUPPOCIRE® A, AS2, AML, and BS2 bases. In one embodiment, the formulation comprises a hard fat suppository base with a high crystallization rate and incorporating phospholipids to facilitate high drug loading. A preferred base is SUPPOCIRE® AML, manufactured by Gattefosse, which includes mono-, di- and triglyceride esters of fatty acids ($C_{10}$ to $C_{18}$), the triester fraction being predominant, and which already contains lecithin and has a hydroxyl value (mg KOH/g)<10 and a melting temperature range of 34 degrees Celsius to 38 degrees Celsius.

In other embodiments, the formulation comprises a pharmaceutically-acceptable excipient that is a water-soluble miscible base. Examples of water-soluble miscible bases include glycerinated gelatins or polyethylene glycol (PEG) polymers (e.g., PEG 300, PEG 1450, PEG 3350, PEG 6000, PEG 8000).

In certain embodiments, the formulation further comprises an additive (e.g., one additive, two or more additives). Additives include, but are not limited to, adsorbents, surface acting agents (e.g., mucosal adhesives, such as xanthan gum, lisinopril, hydroxypropyl methylcellulose, carboxy methylcellulose, and chitosan, among others), viscosity-influencing agents, suspending/dispersing agents (e.g., zinc oxide, alginic acid, crystalline cellulose), plasticizers (e.g., diethylhexyl phthatale, glycerin), melting point-adjusting agents (e.g., white wax), antimicrobial agents (e.g., thimerasol), phospholipides (e.g., lecithin) and antioxidants (e.g., ascorbic acid, ascorbic palmitate, butylated hydroxytoluene (BHT), butylated hydroxyanisole (BHA)).

In some embodiments, the formulation comprises an additive that is an antioxidant. Particular examples of antioxidants that are suitable for inclusion in the formulations described herein include butylated hydroxytoluene (BHT) and butylated hydroxyanisole (BHA), as well as combinations BHT and BHA, in a variety of ratios (e.g., a 1:1 ratio). In a particular embodiment, the formulation comprises butylated hydroxytoluene (BHT). For example, the formulation can comprise about 0.001% to about 0.1%, about 0.005% to about 0.03%, or about 0.0095% to about 0.015% by weight BHT. In a particular embodiment, formulation comprises about 0.01% (e.g., 0.0095%, 0.010%, 0.015%) by weight BHT.

Characteristics of Suppository Formulation

In general, the formulations described herein are solid or semi-solid formulations. Accordingly, in various embodiments, the formulations are suitable for use in a suppository for administration (e.g., rectal administration) to a mammal (e.g., a human). Typically, the formulations described herein have one or more properties (e.g., melting temperature, solubility, stability) that are desirable for suppositories. For example, in some embodiments, the formulation releases the hydrocortisone acetate upon exposure to rectal fluid. Methods for assessing whether a formulation releases the hydrocortisone acetate upon exposure to rectal fluid include, for example, the method exemplified herein.

In additional embodiments, the formulation has a melting temperature in the range of about 35° C. to about 41° C., preferably about 36° C. to about 40° C., more preferably about 37° C. to about 39° C. Methods for determining the melting temperature of a formulation are known in the art and include, for example, the method exemplified herein.

In some embodiments, the formulation is stable (e.g., under storage conditions) at a temperature in the range of about 25° C. to about 40° C. Methods for assessing whether a formulation is stable under storage conditions are known in the art and include, for example, the method exemplified herein.

In other embodiments, a suppository has a weight of about 2 grams (g), which comprises about 90 milligrams (mg) hydrocortisone acetate, and releases at least about 80% of the hydrocortisone acetate at about 180 minutes following exposure to dissolution media comprising a buffered 5% w/v sodium lauryl sulfate solution having a final pH in the range of about 6.8-7.0. In a particular embodiment, the dissolution media comprises 5% w/v sodium lauryl sulfate: acetate buffer pH 5.0 (70:30) final pH adjusted to 6.8-7.0.

Shape and Size of Suppository

The suppositories may be configured to allow for a high level of drug delivery. Alternative configurations of suppositories that allow for easier application into the rectum and can provide greater surface area of the medication for which to expose tissues within the rectum. The suppository can be compact in shape and size for the administration into the body. In some embodiments, the suppository has an oblong shape. In another embodiment, the oblong shape further comprises a cylindrical shape. In other embodiments, the suppository is round, oval or cone-shaped. In certain embodiments, the suppository has a shape that allows contact between the outer surface of the suppository and the mucosal membrane of the rectum when the suppository is situated in the rectum.

Once the suppository is properly placed at a targeted location, the suppository changes shape or composition to administer the medication contained therein. For example, the suppository may dissolve, allowing for the release of the hydrocortisone acetate which acts locally as well as systemically to treat the patient.

In other embodiments, the suppository formulation begins to release the hydrocortisone acetate upon exposure to rectal fluid.

The suppository may be shaped in a manner suitable for administration as further described in U.S. Pat. Nos. 8,192, 393 B2 and 11,298,515 B2, the entire teachings of which are incorporated by reference. In particular, the suppositories may be configured to allow for a high level of drug delivery. Alternative configurations of suppositories that allow for easier application into the rectum and can provide greater surface area of the medication for which to expose tissues within the rectum.

Administration/Delivery of Suppository

An applicator that places medication in the targeted location is the optimal way to treat gastrointestinal diseases such as inflammatory bowel disease, including ulcerative colitis. The applicator is inserted into the anal canal and the suppository is placed in the targeted location in the rectum. The targeted location may be determined based on the condition being treated, such as at the anal-rectal line, just within the rectum, midway inside the rectum, or at the highest point reachable using an applicator. Preferably, the applicator is configured to insert the suppository above an "anal trigger zone" into the rectum to minimize contact of the suppository or its medication with nerves that trigger contraction of anal sphincter muscles that may affect the body's ability to retain and absorb the medication. Applicators and devices for administering suppositories are known in the art and include, for example, those described in U.S. Pat. No. 8,192,393 B2 and U.S. Pat. No. 11,298,515 B2, the contents of which are incorporated herein by reference in their entirety. Such methods and devices are useful for administration of the formulations (e.g., suppositories) described herein. In one embodiment, the suppository is delivered using a single use disposable rectal suppository applicator, such as the Sephure® applicator (disposable single-use suppository applicator, www.sephure.com).

In an embodiment of the invention, a single use applicator allows for a patient to self-administer the suppository to the targeted location once a day for 28 days to treat ulcerative colitis.

Combination Therapies

In some embodiments, the formulations (e.g., suppositories) described herein can be administered in combination with other therapeutic agents that are useful for treating gastrointestinal diseases and disorders. In one embodiment, the formulations (e.g., suppositories) described herein can be administered in combination with mesalamine (e.g., oral mesalamine, a suppository containing mesalamine). In general, the other agent(s) being administered in combination with the hydrocortisone formulations will be administered separately from the hydrocortisone formulation (e.g., in a different form (e.g., a foam, liquid, pill or capsule) or suppository). In some embodiments, the formulations (e.g., suppositories) described herein can be administered in combination with a local anesthetic (e.g., lidocaine).

Kit

In another embodiment, a kit comprises a single 90 mg hydrocortisone acetate suppository and an applicator for delivering the suppository, along with relevant instructions for use to instruct the user how to administer the suppository. The applicator can be any suitable applicator, including a single use applicator as described above.

Selected Specific Embodiments

In addition to the aspects and embodiments disclosed elsewhere herein, the following particular embodiments are contemplated.
1. A method for treating ulcerative colitis comprising administering once a day one suppository comprising about 90 mg hydrocortisone acetate.
2. A method for treating ulcerative colitis comprising administering once a day one suppository comprising about 90 mg hydrocortisone acetate, wherein said one suppository is administered daily in the morning to a patient in need thereof for a period of at least 28 days.
3. A method for treating ulcerative colitis comprising administering once a day one suppository comprising about 90 mg hydrocortisone acetate for a period of time sufficient to achieve remission or reduction of at least one symptom, followed by administering for a period of time at a reduced dose.
4. A method for treating ulcerative colitis comprising administering once a day one suppository comprising about 90 mg hydrocortisone acetate, wherein said one suppository is administered in the morning to a patient in need thereof, followed by administering for a period of time at a reduced dose wherein the reduced dose is administered in the evening.
5. A method for treating ulcerative colitis comprising administering once a day one suppository comprising about 90 mg hydrocortisone acetate, wherein said one suppository is administered in the morning to a patient in need thereof, wherein the patient is suffering from ulcerative colitis.
6. A method for treating ulcerative colitis comprising administering once a day one suppository comprising about 90 mg hydrocortisone acetate and lecithin, wherein said one suppository is administered in the morning to a patient in need thereof.
7. A method for treating ulcerative colitis comprising administering once a day one suppository comprising about 90 mg hydrocortisone acetate and colloidal silicon dioxide, wherein said one suppository is administered in the morning to a patient in need thereof.
8. A method for treating ulcerative colitis comprising administering once a day one suppository comprising about 90 mg hydrocortisone acetate, colloidal silicon dioxide, and saturated C8-C18 triglyceride fatty acids, wherein said one suppository is administered in the morning to a patient in need thereof.
9. A method for treating ulcerative colitis comprising administering once a day one suppository comprising about 90 mg hydrocortisone acetate, colloidal silicon dioxide, and saturated C8-C18 triglyceride fatty acids, wherein said one suppository is administered in the morning to a patient in need thereof, wherein the suppository has a melting temperature range of about 37° C. to about 39° C.
10. A method for treating ulcerative colitis comprising administering once a day one suppository comprising about 90 mg hydrocortisone acetate, colloidal silicon dioxide, and saturated C8-C18 triglyceride fatty acids, wherein said one suppository is administered in the morning to a patient in need thereof, wherein the suppository releases at least about 80% of the hydrocortisone acetate at about 180 minutes following exposure to dissolution media comprising a buffered 5% w/v sodium lauryl sulfate solution having a final pH in the range of about 6.8-7.0.
11. A method of achieving clinical remission in a patient suffering from ulcerative colitis, comprising administering once a day one suppository comprising about 90 mg hydrocortisone acetate, wherein said one suppository is administered to a patient in need thereof.
12. A method of achieving clinical remission in a patient suffering from ulcerative colitis, comprising administering once a day one suppository comprising about 90 mg hydrocortisone acetate to a patient in need thereof.
12. A method of achieving symptomatic relief in a patient suffering from ulcerative colitis, comprising administering once a day one suppository comprising about 90 mg hydrocortisone acetate to a patient in need thereof.
13. A method of achieving clinical remission in a patient suffering from ulcerative colitis, comprising administering once a day in the morning one suppository comprising about 90 mg hydrocortisone acetate.
14. A method of achieving symptomatic relief in a patient suffering from ulcerative colitis, comprising administering once a day in the morning one suppository comprising about 90 mg hydrocortisone acetate.
14. A method of achieving clinical remission in a patient suffering from ulcerative colitis, comprising administering once a day in the morning one suppository comprising about 90 mg hydrocortisone acetate for a period of at least 28 days.
16. A method of achieving symptomatic relief in a patient suffering from ulcerative colitis, comprising administering once a day in the morning one suppository comprising about 90 mg hydrocortisone acetate for a period of at least 28 days.
15. A method of achieving clinical remission in a patient suffering from ulcerative colitis, comprising administering once a day in the morning one suppository comprising about 90 mg hydrocortisone acetate and lecithin for a period of at least 28 days.
18. A method of achieving symptomatic relief in a patient suffering from ulcerative colitis, comprising administering once a day in the morning one suppository comprising about 90 mg hydrocortisone acetate and lecithin for a period of at least 28 days.
16. A method of achieving clinical remission in a patient suffering from ulcerative colitis, comprising administering once a day in the morning one suppository comprising about 90 mg hydrocortisone acetate, lecithin and colloidal silicon dioxide for a period of at least 28 days.
17. A method of achieving clinical remission in a patient suffering from ulcerative colitis, comprising administering once a day in the morning one suppository comprising about 90 mg hydrocortisone acetate, lecithin, colloidal silicon dioxide, and saturated C8-C18 triglyceride fatty acids for a period of at least 28 days.
18. A method of achieving clinical remission in a patient suffering from ulcerative colitis, comprising administering once a day in the morning one suppository comprising about 90 mg hydrocortisone acetate, lecithin, colloidal silicon dioxide, and saturated C8-C18 triglyceride fatty acids for a period of at least 28 days, wherein the suppository has a melting temperature range of about 37° C. to about 39° C.

19. A method of achieving clinical remission in a patient suffering from ulcerative colitis, comprising administering once a day in the morning one suppository comprising about 90 mg hydrocortisone acetate, lecithin, colloidal silicon dioxide, and saturated C8-C18 triglyceride fatty acids for a period of at least 28 days, wherein the suppository releases at least about 80% of the hydrocortisone acetate at about 180 minutes following exposure to dissolution media comprising a buffered 5% w/v sodium lauryl sulfate solution having a final pH in the range of about 6.8-7.0.

20. A kit for treating ulcerative colitis comprising a suppository comprising about 90 mg hydrocortisone acetate, a single use applicator for rectally administering the suppository, and instructions for the patient to self-administer said suppository using the single use applicator with the suppository.

21. A method for treating ulcerative colitis and reducing the stool frequency of a patient comprising administering once a day in the morning one suppository comprising about 90 mg hydrocortisone acetate to a patient in need thereof.

22. A method for treating ulcerative colitis and reducing the stool frequency of a patient comprising administering once a day in the morning one suppository comprising about 90 mg hydrocortisone acetate to a patient in need thereof for a period of 28 days.

23. A method for treating ulcerative colitis and reducing the rectal bleeding in a patient comprising administering once a day in the morning one suppository comprising about 90 mg hydrocortisone acetate to a patient in need thereof.

24. A method for treating ulcerative colitis and reducing the rectal bleeding in a patient comprising administering once a day in the morning one suppository comprising about 90 mg hydrocortisone acetate to a patient in need thereof for a period of 28 days.

25. A method for treating ulcerative colitis, reducing stool frequency, and reducing the rectal bleeding in a patient comprising administering once a day in the morning one suppository comprising about 90 mg hydrocortisone acetate to a patient in need thereof.

26. A method for treating ulcerative colitis, reducing stool frequency, and reducing the rectal bleeding in a patient comprising administering once a day in the morning one suppository comprising about 90 mg hydrocortisone acetate to a patient in need thereof for a period of 28 days.

27. A method for reducing one or more symptoms of ulcerative colitis in a patient comprising administering once a day in the morning one suppository comprising about 90 mg hydrocortisone acetate to a patient in need thereof, wherein the symptom is selected from frequent bowel movements, diarrhea, tenesmus, urgency, rectal bleeding, rectal pain, abdominal pain, cramping, fever, fatigue, loss of appetite, and weight loss.

28. A method for reducing two or more symptoms of ulcerative colitis in a patient comprising administering once a day in the morning one suppository comprising about 90 mg hydrocortisone acetate to a patient in need thereof, wherein the symptom is selected from frequent bowel movements, diarrhea, tenesmus, urgency, rectal bleeding, rectal pain, abdominal pain, cramping, fever, fatigue, loss of appetite, and weight loss.

29. A method for reducing three or more symptoms of ulcerative colitis in a patient comprising administering once a day in the morning one suppository comprising about 90 mg hydrocortisone acetate to a patient in need thereof, wherein the symptom is selected from frequent bowel movements, diarrhea, tenesmus, urgency, rectal bleeding, rectal pain, abdominal pain, cramping, fever, fatigue, loss of appetite, and weight loss.

30. A method for reducing four or more symptoms of ulcerative colitis in a patient comprising administering once a day in the morning one suppository comprising about 90 mg hydrocortisone acetate to a patient in need thereof, wherein the symptom is selected from frequent bowel movements, diarrhea, tenesmus, urgency, rectal bleeding, rectal pain, abdominal pain, cramping, fever, fatigue, loss of appetite, and weight loss.

31. A method of improving the Quality of Life of a patient suffering from ulcerative colitis as determined by the responses to the Inflammatory Bowel Disease Questionnaire (IBDQ) validated questionnaire, completed by the patient, administering once a day in the morning one suppository comprising about 90 mg hydrocortisone acetate to a patient in need thereof for a period of 28 days, and repeating the patient responses to a second IBDQ questionnaire completed by the patient after the 28 day period.

32. A method for reducing the Disease Activity Score (DAI) according to the Mayo Score of severity grading of a patient suffering from ulcerative colitis comprising administering once a day in the morning one suppository comprising about 90 mg hydrocortisone acetate to a patient in need thereof, wherein the DAI grading is based on a reduction of at least one or more symptoms selected from endoscopic assessment by an medical professional, frequent bowel movements, diarrhea, tenesmus, urgency, rectal bleeding, rectal pain, abdominal pain, cramping, fever, fatigue, loss of appetite, and weight loss.

33. A method for reducing the symptoms of ulcerative colitis of a patient comprising administering once a day in the morning one suppository comprising about 90 mg hydrocortisone acetate to a patient in need thereof.

34. A method for treating ulcerative colitis comprising administering once a day one suppository comprising about 90 mg hydrocortisone acetate, wherein said one suppository is administered to a patient in need thereof.

35. A method for treating ulcerative colitis comprising administering once a day one suppository comprising about 90 mg hydrocortisone acetate, wherein said one suppository is administered daily in the evening to a patient in need thereof.

36. A method for treating ulcerative colitis comprising administering once a day one suppository comprising about 90 mg hydrocortisone acetate, wherein said one suppository is administered daily in the evening to a patient in need thereof for at least 28 days.

Embodiments of the invention will now be illustrated by examples. The examples are not intended to be limiting of the scope. In conjunction with the detailed and general description above, the examples provide further understanding of embodiments of the present invention and an outline of a process for preparing formulations of the invention and practicing the methods of embodiments of the invention.

EXAMPLES

Example 1: Study to Evaluate the Safety and Efficacy of Hydrocortisone Acetate Suppositories Summary:

A randomized, multi-center, double-blind, three arm placebo-controlled study in male and non-pregnant, non-lactating female subjects aged 18 years to examine the safety and efficacy of two dosing regimens of hydrocortisone acetate 90 mg suppository administered with the Sephure applicator for the treatment of ulcerative colitis of the rectum.

Detailed Description:

Hydrocortisone acetate 90 mg or placebo will be administered as a rectal suppository with a Sephure® suppository applicator. Two arms of the study will receive different dosage regimens of hydrocortisone acetate, and the third arm will receive placebo. All subjects will administer the study drug twice a day; once in the morning and once in the evening for 28 days.

The study population will consist of male and non pregnant, non lactating females aged 18 years and older with a confirmed diagnosis of active UC of the rectum.

Treatment Arms:
  Combination Product: Twice daily 90 mg hydrocortisone acetate suppository administered with Sephure applicator
  Combination Product: Once daily 90 mg hydrocortisone acetate or placebo suppository administered with Sephure applicator
  Combination Product: Twice daily placebo suppository administered with Sephure applicator Eligibility Criteria:
  Inclusion Criteria:
    Male or non pregnant, non lactating females aged 18 years and older.
    Subjects with a confirmed diagnosis of active UC of the rectum, extending no more than 15 centimeters (cm) (5.9 inches) proximal to the anal verge as assessed by colonoscopy performed at Visit 2. Note: Subjects may have a history of more extensive UC (e.g., pancolitis), but have active disease only in the rectum at the time of enrollment.
    Modified Mayo sub score for stool frequency of 1-3.
    Modified Mayo sub score for rectal bleeding of 0-2.
    Modified Mayo endoscopic sub score of 2-3.
    Total Modified Mayo Score (without physician global assessment) of 4-8.

Exclusion Criteria:—
  History or current diagnosis of bacterial or other infectious colitis, radiation enteritis and radiation proctitis, Crohn's disease, collagenous colitis and indeterminate colitis.
  Prior gastrointestinal surgery except appendectomy, cholecystectomy, and hernia.
  Concomitant active lower gastrointestinal disease (except Irritable Bowel Syndrome) or distortion of intestinal anatomy.
  Bleeding hemorrhoids at the time of enrollment.
  Acute diverticulitis at the time of enrollment.
  Acute or chronic pancreatitis at the time of enrollment.
  Unmanaged celiac disease at the time of enrollment.
  Positive stool test for enteric pathogens, *Clostridium difficile*, or presence of ova and parasites.
  Taking a prohibited medication.

Primary Outcome Measurements

To evaluate the efficacy of the two dosage regimens of the study drug over a 28 day period, the clinical remission outcome was measured using the Modified Mayo Score.

Secondary Outcome Measurements

To assess the change in stool frequency over the 28 day period, the reduction of stool frequency was measured using Mayo scoring sub score of stool frequency.

To assess the change in rectal bleeding over a 28 day period, the rectal bleeding was measured using Mayo Scoring sub-score of rectal bleeding equal to 0.

Other Outcome Measurements

To examine the quality of life of patients over the 28 day period, a Qualify of Life assessment was measured using IBDQ validated questionnaire.

To assess disease severity over the 28 day period, a grading of the disease severity was measured using Mayo scoring sub-sore of Physician's Global Assessment.

To evaluate the exposure of hydrocortisone acetate levels of safety over the 28 day period, concentrations of hydrocortisone acetate was measured using pharmokinetic sampling.

Primary Efficacy Endpoint

The Phase 3 study evaluated Day 29 clinical remission (CR) as the primary efficacy endpoint.

197 subjects were randomized: Placebo (n=66), QD (n=65), and BID (n=66).

To allow for the two active group comparisons, two-sided p=0.025 was required.
  Prospective rules (BDRM) excluded 26 endocrinology cases
  Primary analysis: 171 subjects include 6 cases missing Day 29 endoscopy
  Supportive analysis: 165 subjects excluding those with missing endoscopy Primary Analysis: N=171 imputation using baseline characteristics
  Stratified by baseline factors: Region, user/non-user status, gender
  Multiple imputation applied with 25 simulations run to compare QD & BID vs Placebo
  Each simulation was analyzed using logistic regression
  For each comparison vs Placebo, two-sided p=0.025 was required.

Supportive Analysis: N=165 without imputation without stratification
  Results were analyzed using a two-sided Fisher Exact test. For each comparison vs
  Placebo, two-sided p=0.025 was required.
  Results presented for both the primary and supportive analysis for the primary endpoint

TABLE 1

| | Primary Analysis: N = 171 With Imputation | |
|---|---|---|
| | Treatment Group | |
| Result | QD | BID |
| Risk ratio (vs Placebo) | 2.217 | 2.039 |
| 2-sided p-value | 0.0098√ | 0.0192√ |
| Conclusion | Two-sided p < 0.025 met for both BID and QD | |

TABLE 2

Supportive Analysis: N = 165 Without Imputation

| Result | Treatment Group | | |
|---|---|---|---|
| | Placebo | QD | BID |
| CR % (rate) | 2.1% (1/47) | 23.3% (14/60) | 19.0% (11/58) |
| 2-sided p-value | — | 0.0105√ | 0.0191√ |
| Conclusion | Two-sided p < 0.025 met for both BID and QD | | |

In conclusion, the primary efficacy to treat ulcerative colitis was met for both QD and BID groups. Less than 4% of primary efficacy endpoint had to be imputed. In particular, 6/171 (3.5%) required Day 29 endoscopy imputation. In addition, preliminary data indicated a lower adverse event score associated with the QD group. Additional results from the clinical trials include the following findings. The primary endpoint called for patients to meet an average score between 0 and 2 on the Mayo score, with 0 representing an unaffected person. In the trial, 171 patients were split into three arms with one receiving either once-daily or twice-daily dosing of the 90 mg hydrocortisone acetate suppository, or placebo for 28 days. Results from the trial saw 23.0% of patients in the single dose arm achieving clinical remission by day 29. In the twice-daily treatment arm, 17.5% of patients achieved clinical remission. In the placebo group, only 2.1% of patients saw remission. Additionally, the trial met its secondary endpoint by cutting the score for rectal bleeding down to an average of 0 across all groups by day 15, alongside similar results in the reduction of stool frequencies.

Consistent p-values were achieved with and without imputation:

Placebo vs QD: 0.0098 (imputation) vs 0.0105 (without imputation)
Placebo vs BID: 0.0192 (imputation) vs 0.0191 (without imputation)

Example 2: Development and Characterization of Hydrocortisone Acetate Formulations Containing Colloidal Silicon Dioxide Studies relating to the development and characterization of hydrocortisone acetate formulations containing colloidal silicon dioxide have been previously described in U.S. application Ser. No. 15/555,325, which is herein incorporated by reference in its entirety. The composition of preferred suppository formulations are Prototype 11 containing 94.8% w/w SUPPOCIRE® AML, 0.7% w/w colloidal silicon dioxide, and 4.5% w/w hydrocortisone acetate and Prototype 15 containing 94.8% w/w Wiepsol H-15, 0.7% w/w colloidal silicon dioxide, and 4.5% w/w hydrocortisone acetate. Prototype 11 is the preferred formulation, which includes hydrocortisone acetate 90 mg, colloidal silicon dioxide 14 mg and SUPPOCIRE® AML 1896 mg, which provides a suppository with a total weight of 2 g. This formulation was then subjected to physical and chemical stability, and dissolution studies.

Physical and Chemical Stability Studies of the Formulation

Prototype 11 (hydrocortisone acetate 90 mg, colloidal silicon dioxide 14 mg and SUPPOCIRE® AML 1896 mg) was subjected to physical and chemical stability studies. The study employed two storage conditions in order to demonstrate compatibility with the selected excipients and to give confidence that the formulations are appropriate for longer storage. The conditions include:

25±2° C. / 60±5% RH (relative humidity)=standard storage conditions
40±2° C. / 75±5% RH (relative humidity)=accelerated storage conditions The results of the physical and chemical stability studies showing the assay and impurity results for SUPPOCIRE® AML active prototypes under storage conditions (standard and accelerated) were previously summarized in U.S. application Ser. No. 15/555,325, which is herein incorporated by reference. The results from the initial and one-month through three-month stability studies for prototype 11 showed negligible amounts of total impurities after three months of storage. In particular, the total impurities at T=3 month stored at 25° C./60% RH was 0.23 and at T=3 months stored at 40° C./75% RH was 0.16. These studies demonstrate that prototype 11 remained stable for at least three months under the conditions tested.

Dissolution Studies

The selected prototype 11 (hydrocortisone acetate 90 mg, colloidal silicon dioxide 14 mg and SUPPOCIRER AML 1896 mg) was next subjected to dissolution studies (Table 5). Samples stored at both 25° C./60% RH and 40° C./75% RH were subjected to the dissolution testing. Samples stored at 25° C./60% RH were subjected to dissolution testing at initial (Time (T)=O), 1 month (T=1) and 2 months (T=2) of storage. Samples stored at both 25° C./60% RH and 40° C./75% RH were subjected to testing at 3 months (T=3) and 7 months (T=7) of storage. The methods for the dissolution studies were previously described in U.S. application Ser. No. 15/555,325. The results of the dissolution studies showed that the dissolution profile for hydrocortisone acetate remains consistent even after 7 months of storage at standard storage conditions (25° C./60% RH). However, storage at accelerated conditions (40° C./75% RH) after 7 months resulted in a decrease of hydrocortisone acetate release from the lead formulation.

Example 3: Hydrocortisone Acetate (90 mg) Suppository Specification and Dissolution Profile The specification and dissolution profile for the 2 gram suppository containing 90 mg of hydrocortisone acetate and colloidal silicon dioxide (prototype 11) was previously disclosed in U.S. application Ser. No. 15/555,325.

The hydrocortisone acetate (90 mg) suppository was packaged in 2 gram polyethylene/polyvinyl chloride (PE/PVC) suppository shells and subjected to standard CQAs for 60 days under 40° C./75% RH storage conditions. The appearance, melting temperature and stability of the 2 g suppository hydrocortisone acetate 90 mg remained constant and virtually unchanged after 60 days of storage under accelerated conditions (40° C./75% RH). Total impurities that were generated over a period of 60 days remained negligible (<0.05%) under accelerated storage conditions (40° C./75% RH). Moreover, the dissolution studies under our standard protocol have also shown that the 2 g suppository releases at least about 80% of the hydrocortisone acetate at about 180 minutes following exposure to dissolution media comprising 5% w/v sodium lauryl sulfate: acetate buffer pH 5.0 (70:30) final pH adjusted to 6.8-7.0. At about 360 minutes following exposure to dissolution media comprising 5% w/v sodium lauryl sulfate: acetate buffer pH 5.0 (70:30) final pH adjusted to 6.8-7.0, the 2 g suppository releases at least about 97% of the hydrocortisone acetate.

Example 4: Manufacturing Process for
Hydrocortisone Acetate Suppository Formulation The prototype 11 (both active and placebo) was subjected to stability studies at two different conditions: 1) 25° C./60% RH; and 2) 40° C./75% RH.

Preparation of the base: The stainless steel vessel identification number and tare weight was recorded. Into the vessel, was add the weighed amount of base and begin melting the base using a hot stir plate and water bath, low shear sweep/side scrape mixing (hand mix was used in the lab for small scale operations) until all the base was completely melted. The temperature was maintained at 55±5° C. (Tf).

Addition of colloidal silicon dioxide: A silverson mixer (or similar homogenizer) was set up. The required amount of colloidal silicon dioxide was weighed and added to the melted base. The colloidal silicon dioxide was then allowed to hydrate by mixing using a square shape mesh. The mixing speed was maintained between 3000-3500 RPM. The temperature was maintained at 55±5° C. (Tf).

Addition of hydrocortisone acetate: The required amount of hydrocortisone acetate was weighed and added to the main batch while mixing with homogenizer set at 4000-4500 RPM and equipped with a square shape mesh for ten minutes or until visibly uniformly dispersed. The temperature was maintained at 55±5° C. (Tf).

Filling process: Begin mixing the batch using a propeller type mixer (e.g. IKA) at 500-1500 RPM. The suspended hydrocortisone acetate must be kept from settling during the filling operation. Maintain batch temperature between 50-60° C. Set up a peristaltic pump (or similar) along with the tubing and adjust the settings so that it dispenses two grams of product in each cycle. The tubing was maintained at 50-60° C. with the help of a heat tape to avoid product congealing in the tube during filling into the suppositories. Dispense one cycle of product into each suppository form and allow to cool to room temperature. The cooling process may be accelerated by placing the filled forms into a cooling tunnel (or equivalent).

The relevant teachings of all patents, published applications and references cited herein are incorporated by reference in their entirety.

While aspects of this invention have been particularly shown and described with references to example embodiments thereof, it will be understood by those skilled in the art that various changes in form and details may be made therein without departing from the scope of the invention encompassed by the appended claims of this provisional application or a later-filed non-provisional application claiming priority hereto.

What is claimed is:

1. A method for treating ulcerative colitis comprising rectally administering once a day a single suppository comprising about 90 mg hydrocortisone acetate for a period of time sufficient to achieve remission or reduction of a symptom and followed by a period of administering a reduced dosage.

2. The method as claimed in claim 1, wherein the one suppository is administered in the morning to a patient in need thereof daily for a period of at least 28 days.

3. The method as claimed in claim 1, wherein the suppository comprises lecithin.

4. The method as claimed in claim 3, wherein the suppository comprises colloidal silicon dioxide.

5. The method as claimed in claim 4, wherein the suppository comprises an oleaginous base.

6. The method as claimed in claim 5, wherein the suppository has a melting temperature range of about 37° C. to about 39° C.

7. The method as claimed in claim 5, wherein the suppository releases at least about 80% of the hydrocortisone acetate at about 180 minutes following exposure to dissolution media comprising a buffered 5% w/v sodium lauryl sulfate solution having a final pH in the range of about 6.8-7.0.

8. The method of achieving clinical remission in a patient suffering from ulcerative colitis, comprising rectally administering once a day a single suppository comprising about 90 mg hydrocortisone acetate to a patient in need thereof.

9. The method as claimed in claim 8, wherein said suppository is administered to the patient in the morning.

10. The method as claimed in claim 8, wherein said suppository is administered daily to the patient in the morning for a period of at least 28 days.

11. The method as claimed in claim 10, wherein the suppository comprises lecithin.

12. The method as claimed in claim 10, wherein the suppository comprises colloidal silicon dioxide.

13. The method as claimed in claim 12, wherein the suppository comprises an oleaginous base.

14. The method as claimed in claim 13, wherein the suppository has a melting temperature range of about 37° C. to about 39° C.

15. The method as claimed in claim 14, wherein the suppository releases at least about 80% of the hydrocortisone acetate at about 180 minutes following exposure to dissolution media comprising a buffered 5% w/v sodium lauryl sulfate solution having a final pH in the range of about 6.8-7.0.

16. The method as claimed in claim 1, wherein the period of administering a reduced dose is about 10 days.

17. The method of claim 16, wherein the reduced dose is achieved by administering the suppository once every other day.

18. The method as claimed in claim 8, wherein following remission the suppository is administered for a period of time at a reduced dose.

19. The method of claim 18, wherein the period of administering a reduced dose is about 10 days.

20. The method of claim 19, wherein the reduced dose is achieved by administering the suppository once every other day.

21. A method for treating ulcerative colitis comprising rectally administering once a day in the morning a single suppository comprising greater than about 90 mg hydrocortisone acetate and up to about 180 mg hydrocortisone acetate for a period of time sufficient to achieve remission or reduction of a symptom.

22. The method of claim 1, wherein the administering once a day a single suppository comprising about 90 mg hydrocortisone acetate is in the morning, and wherein the administering of a reduced dosage occurs in the evening.

23. The method of claim 22, wherein the reduced dosage is accomplished by administering a single suppository comprising about 90 mg hydrocortisone acetate while skipping administration on one or more days during the reduced dosage period.

24. The method of claim 22, wherein the reduced dosage is accomplished by administering a single suppository comprising an amount of hydrocortisone acetate that is less than about 90 mg.

25. The method as claimed in claim 21, wherein following remission the suppository is administered for a period of time at a reduced dose.

26. The method of claim 25, wherein the period of administering a reduced dose is about 10 days.

27. The method of claim 26, wherein the reduced dose is achieved by administering the suppository once every other day.

28. The method as claimed in claim 21, wherein the suppository comprises lecithin.

29. The method as claimed in claim 21, wherein the suppository comprises colloidal silicon dioxide.

30. The method as claimed in claim 21, wherein the suppository comprises about 90 mg of hydrocortisone acetate.

* * * * *